United States Patent [19]
Forney

[11] Patent Number: 5,165,540
[45] Date of Patent: Nov. 24, 1992

[54] ANGIOGRAPHIC CATHETER PACKAGE

[75] Inventor: LeRoy S. Forney, St. Louis, Mo.

[73] Assignee: Sherwood Medical Company, St. Louis, Mo.

[21] Appl. No.: 463,092

[22] Filed: Jan. 10, 1990

[51] Int. Cl.$^5$ .................................. B65D 83/10
[52] U.S. Cl. .................................. 206/364; 206/363; 206/438; 206/470
[58] Field of Search ............ 206/363, 364, 438, 486, 206/470, 471, 564, 563, 562, 303, 63.3; 604/280, 281

[56] References Cited

U.S. PATENT DOCUMENTS

| | | | |
|---|---|---|---|
| Re. 29,343 | 8/1977 | Amplatz | 53/21 FC |
| 3,035,691 | 5/1962 | Rasmussen et al. | 206/364 |
| 3,104,172 | 9/1963 | Wizelman | 206/471 |
| 3,338,401 | 8/1967 | Regan, Jr. | 206/63.3 |
| 3,606,001 | 9/1971 | Talonn et al. | 206/63.2 |
| 3,612,038 | 10/1971 | Halligan | 206/364 |
| 3,633,758 | 1/1972 | Morse et al. | 211/13 |
| 3,910,410 | 10/1975 | Shaw | 206/471 |
| 3,972,418 | 8/1976 | Schuler et al. | 206/63.3 |
| 3,983,996 | 10/1976 | Hendren | 206/363 |
| 4,005,776 | 2/1977 | Seeley | 206/306 |
| 4,019,633 | 4/1977 | Roth | 206/364 |
| 4,230,115 | 10/1980 | Walz, Jr. et al. | 206/438 |
| 4,256,225 | 3/1981 | Jackson | 206/363 |
| 4,262,800 | 4/1981 | Nethercutt | 206/364 |
| 4,332,322 | 6/1982 | Jaeschke et al. | 206/364 |
| 4,366,901 | 1/1983 | Short | 206/364 |
| 4,779,727 | 10/1988 | Taterka et al. | 206/364 |
| 4,807,747 | 2/1989 | Hadtke | 206/471 |
| 4,823,167 | 4/1989 | Manska et al. | 206/364 |
| 4,923,061 | 5/1990 | Trombley, III | 206/364 |
| 4,925,448 | 5/1990 | Bazaral | 206/364 |

FOREIGN PATENT DOCUMENTS 961452 1/1975 Canada ....................... 206/380

Primary Examiner—David T. Fidei
Attorney, Agent, or Firm—Montgomery W. Smith; Richard D. Allison; Curtis D. Kinghorn

[57] ABSTRACT

The present invention relates to an angiographic catheter package consisting of a sterilizable envelope pouch, an elongate tray and a catheter tip restraint which releasably retains the catheter tip therein in the desired performed shape. The tip restraint securely holds the catheter tip in the desired shape during sterilization and storage of the catheter and yet readily releases the catheter tip from the tip restraint when the user desires to remove the catheter from the sterile package.

19 Claims, 5 Drawing Sheets

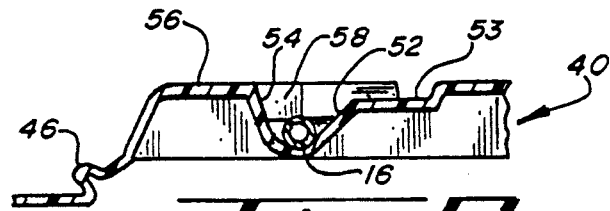
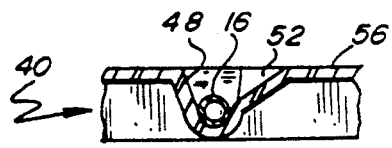
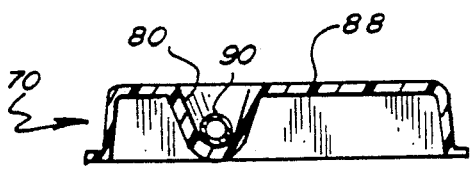
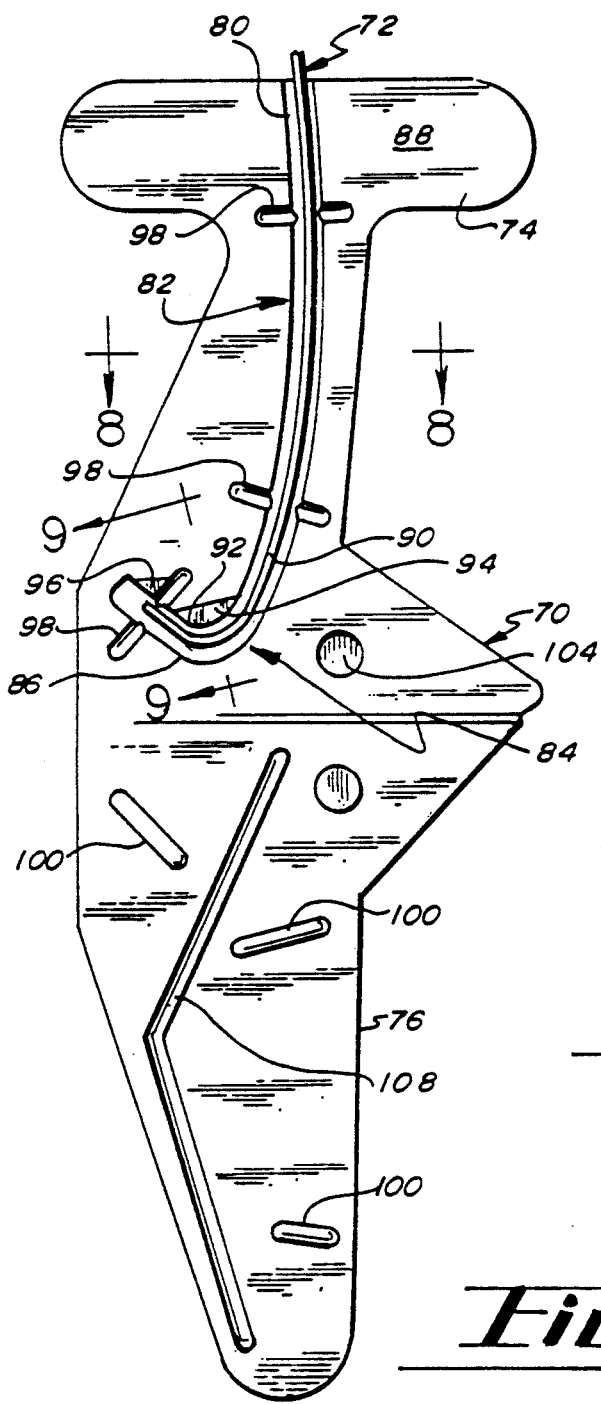
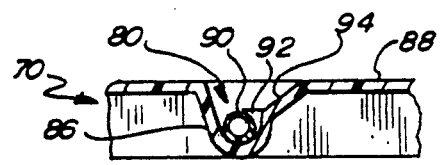

ANGIOGRAPHIC CATHETER PACKAGE

FIELD OF THE INVENTION

This invention relates to a catheter package and more particularly to an angiographic catheter package including a catheter tip restraint particularly adapted to maintain the desired catheter tip shape during sterilization and storage of the angiographic catheter.

BACKGROUND OF THE INVENTION

In the field of angiography, a variety of shapes and sizes of preformed catheters have been developed so that the catheter will enter the desired blood vessel once the catheter has been inserted into the vascular system of a patient. Angiographic catheters must have sufficient flexibility to follow a tortuous route into the desired position in the vascular system, but must also take on a predetermined shape once the catheter has been positioned in the vascular system so that the catheter may then be manipulated into the desired blood vessel.

Although angiographic catheters are formed having very specific shapes and sizes during the manufacturing process, the overall shape of the catheter will oftentimes change during the subsequent sterilization process and during storage of the catheter. For example, during ethylene oxide gas sterilization of an angiographic catheter, the long shaft section of the catheter will oftentimes increase in length while the preformed shape of the catheter tip will oftentimes relax. The amount of change in shape or length caused by the sterilization process or during storage of the catheter will vary between each individual catheter and therefore, it is impractical to attempt to shape the catheter during the manufacturing process to account for any subsequent change in the length or shape of the catheter caused by the sterilization process or storage of the catheter.

One approach to maintaining the desired shape of the catheter during sterilization or storage is to insert a bendable, nonresilient wire through the center of a section of catheter tubing. A physician or technician then physically bends the wire and catheter combination into the desired shape prior to sterilization. Unfortunately, there is no effective way to determine the action of the sterilizing gas on bacteria which may be located between the interior of the catheter and the stiffening wire. Additionally, the additional cost and time required by this approach makes it commercially unacceptable.

A further approach is disclosed in U.S. Pat. No. Re. 29,343 granted to Amplatz on Aug. 7, 1977. The approach disclosed in the Amplatz patent requires the use of a forming board which has a groove formed therein identical to the desired shape and length of the catheter. The cross-sectional shape of the groove is described as being wider at the bottom and narrower at the open top of the groove where it becomes a part of the flat top surface of the forming board to allow a length of thermoplastic tubing to be initially placed and retained in the groove. The forming board and catheter combination are then heated to a temperature sufficient to mold and shape the catheter to the contour of the groove in the forming board. When the forming board and catheter combination are cooled, the catheter will retain the desired shape of the groove in the forming board. Next, the forming board and catheter are placed in a sealable plastic envelope which is then sterilized and stored until the catheter is ready for use.

The forming board disclosed in the Amplatz patent does not accommodate changes in the length of the shaft section of the catheter which may occur during sterilization or storage of the catheter. If the shaft section of the catheter increases in length during sterilization or storage, the catheter tip may be forced out of the distal end of the forming board. If the shaft section of the catheter decreases in length during sterilization or storage, the catheter tip may be drawn proximally through the groove in the forming board to alter the final shape of the catheter tip.

Another approach is illustrated by a Judkins-type of catheter marketed by the Diagnostic Products Division of Mallinkrodt Inc. located in St. Louis, Mo. U.S.A. wherein a preformed catheter is placed in a plastic tray and the shaft section of the catheter is held loosely in a groove in the plastic tray. The plastic tray includes tabs molded into the top surface of the groove to retain the catheter shaft in position within the tray. There is nothing in the package to retain the catheter tip in the desired shape. Another approach to the packaging of an angiographic catheter is represented by the currently marketed femoral Judkins-type of right coronary angiographic catheter manufactured by the Cordis Corporation of Miami, Fla., U.S.A., which uses a cardboard type of support for the catheter shaft. Tabs on the cardboard support retain the shaft section of the catheter in the desired position within the package. A small plastic bag is placed on the catheter tip to maintain the desired shape of the catheter tip. In the pigtail type of angiographic catheter manufactured by the Cordis Corporation, the plastic bag is replaced by a tubular plastic sheath which requires the user to straighten the catheter tip by manually removing the catheter tip from the sheath prior to the use of this type of angiographic catheter.

The foregoing approaches do not always maintain the desired shape of the preformed catheter after sterilization or during storage of the packaged catheter. Therefore, a relatively significant number of improperly shaped catheters must be discarded or reshaped after sterilization. Additionally, improperly shaped catheters may be returned to the manufacturer by the user as being defective even though the integrity of the catheter package has been maintained.

SUMMARY OF THE PRESENT INVENTION

An object of the present invention is to provide an angiographic catheter package which will maintain the desired shape of the preformed catheter after sterilization and during storage of the angiographic catheter.

Another object of the present invention is to provide an angiographic catheter package which will accommodate variations in the length of the catheter shaft and will allow the length of the catheter shaft to change during sterilization without affecting the shape of the catheter tip.

A further object of the present invention is to provide an angiographic catheter package which is inexpensive to manufacture and allows the angiographic catheter to be readily removed therefrom.

In accordance with the preferred form of the present invention, the angiographic catheter package includes a conventional sterilization pouch which encloses an elongate plastic tray with distal and proximal pockets on the ends thereof and at least one elongate and linear groove therebetween. A catheter tip restraint is longitudinally slidable in the distal pocket of the tray. The tip restraint is preferably a hinged thermoformed plastic insert having a base section which includes an elongate and curved channel having at least one perimeter wall formed similar to the desired shape of the preformed catheter tip. The tip restraint also preferably includes bevelled surfaces selectively positioned along the proximal side surface of the channel to facilitate the removal of the catheter tip from the tip restraint without substantially deforming the catheter tip. Other sections of the perimeter wall are perpendicular to the top surface of the base section to prevent the catheter from inadvertently sliding forwardly out of the channel if the length of the shaft section of the catheter increases during sterilization or storage of the catheter. The tip restraint also includes a plurality of female recesses on the base section thereof which receive male tabs from the cover section of the tip restraint to retain the catheter tip positioned in the channel when the cover section of the tip restraint is folded over the top surface of the base section. Additionally, one or more male closure tabs are positioned on the cover section near the hinged section of the tip restraint to cooperate with similarly oriented female closure tabs on the base section of the tip restraint to provide a limited amount of resistance to the unfolding of the tip restraint and to prevent the catheter tip from becoming displaced from the tip restraint during sterilization or storage of the angiographic catheter package.

An advantage of the present invention is that the catheter package of the present invention maintains the desired shape of the angiographic catheter while allowing the angiographic catheter to be readily removed therefrom.

A further advantage of the present invention is that the catheter tip restraint is readily adaptable for use with nearly any catheter tip shape.

A further advantage of the present invention is that the catheter package allows the user to visually inspect the shape of the catheter prior to use without removing the catheter from the package.

A further advantage of the present invention is that the thickness of the tip restraint is approximately equal to the depth of the tray pocket so that movement of the cover section of the tip restraint is limited by the conventional sterilization pouch.

A further advantage of the present invention is that the hinge of the tip restraint is designed to assist in opening the cover section of the tip restraint when the user desires to remove the catheter from the package.

BRIEF DESCRIPTION OF THE DRAWINGS

FIG. 1A is an enlarged frontal elevation view of the present invention as illustrated in FIG. 1, portions of which have been cut away;

FIG. 5 is a side cross-sectional view of the type of tip restraint illustrated in FIG. 2 taken along lines 5—5 of FIG. 3;

FIG. 6 is a side cross-sectional view of the type of tip restraint illustrated in FIG. 2 taken along lines 6—6 of FIG. 3;

FIG. 7 is a frontal view of an unfolded tip restraint of the present invention adapted for use with an Internal Mammary Artery Bypass type of angiographic catheter;

FIG. 8 is a side cross-sectional view of the tip restraint illustrated in FIG. 7 taken along lines 8—8 of FIG. 7;

FIG. 9 is a side cross-sectional view of the tip restraint illustrated in FIG. 7 taken along lines 9—9 of FIG. 7;

DETAILED DESCRIPTION OF THE INVENTION

The invention disclosed herein is intended to be used in conjunction with an angiographic catheter; however, it is anticipated that the present invention may be modified for use with nearly any catheter or medical tubing, without departing from the contemplated scope of the present invention as defined by the claims attached hereto.

As illustrated in the attached drawings, the present invention relates to an improvement in the packaging of a catheter to allow the overall length of the catheter to fluctuate during sterilization and storage while maintaining the desired preformed shape of the catheter and catheter tip. FIGS. 1-6 illustrate the present invention adapted for use with a left Amplatz type of catheter designated generally herein as catheter 10. This type of catheter 10 is typically used to visualize the left coronary artery of a patient's heart and generally includes a hub fitting 12 on the proximal end of the catheter 10 and a generally straight shaft section 14 which extends between the hub fitting 12 and a distally positioned catheter tip 16. The catheter tip 16 of the present embodiment includes a primary curvature section and a distally located secondary curvature section, both of which are particularly designed to facilitate the placement of the catheter into the left ventricle of a patient's heart.

Figure 1:
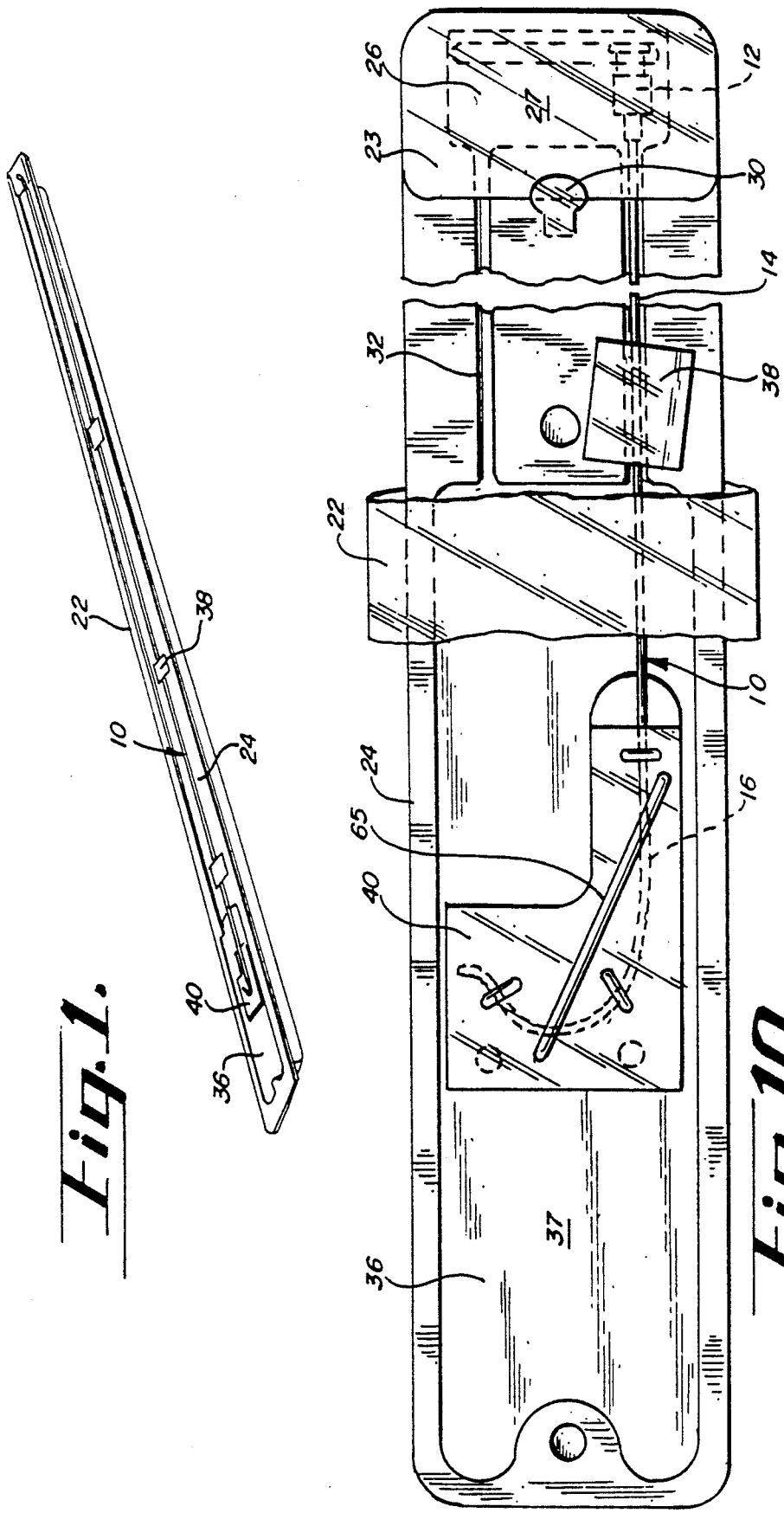
FIG. 1 is a frontal perspective view of the present invention adapted for use with a left Amplatz type of angiographic giographic catheter enclosed in a conventional sterilization pouch, portions of which have been cut away.

As illustrated in FIGS. 1 and 1A, the catheter 10 is sterilely packaged in a conventional type of envelope pouch 22 consisting of a transparent polycarbonate film which is hermetically sealed to a spun polypropylene backing. The envelope pouch 22 encloses an elongate thermoformed tray 24 which is designed to hold various shapes and sizes of angiographic catheters in the linear channel 32 during sterilization, shipping and storage. The tray 24 includes a proximally located proximal pocket 26 having a recessed and flat base surface 27 and a hinged cover sheet 28 adapted to be folded over the proximal pocket 26. The hinged cover sheet 28 loosely retains the hub fitting 12 of the catheter in the proximal pocket 26 of the tray 24 when the end of the cover sheet 28 is placed in a tab member 30 located near the distal of the proximal pocket 26.

A pair of elongate and linear channels 32 extend distally from the proximal pocket 26 to a larger and distally located distal pocket 36. The distal pocket 36 includes a recessed and flat base surface 37. As illustrated in FIG. 1, a plurality of retaining tabs 38 extend across one of the linear channels 32 to retain the shaft section 14 of the catheter 10 therein. The location and placement of the retaining tabs 38 along the linear channel 32 varies depending on the type of catheter 10 being inserted into the tray 24. As illustrated in FIGS. 1 and 1A, when a Left Amplatz type of catheter is inserted into the tray 24, the shaft section 14 of the catheter 10 is preferably placed in the lower linear channel 32 and the retaining tabs 38 are evenly spaced along the outer edge of the linear channel 32. When an Internal Mammary Artery type of catheter, as illustrated in FIGS. 7-9, is inserted into the tray 24, the upper linear channel 32 is preferably used to retain the shaft section of the catheter therein. The retaining tabs 38 are positioned adjacent to the upper linear channel 32 so that the two proximal most retaining tabs 38 are adhesively bonded from the inner edge of the upper linear channel 32 and are evenly spaced from the proximal pocket 26. The third retaining tab 38 is adhesively bonded from the outer edge of the upper linear channel 32 and is positioned approximately one-half of the distance from the distal pocket 36 as compared to the distance between the other retaining tabs 38. The relative spacing of the retaining tabs 38 and the respective desired linear channel 32 are chosen to provide the least amount of resistance to the removal of the catheter 10 from the tray 24 while ensuring that the catheter tip 16 will not be deformed as the catheter 10 is removed from the tray 24 and the tip restraint 40, the structure and function of which will be described more fully hereinafter.

As illustrated in FIGS. 1 and 1A, the tip restraint 40 of the preferred embodiment is longitudinally slidable within the distal pocket 36 of the tray 24 to allow the shaft section 14 of the catheter 10 to expand or contract during sterilization and storage of the catheter 10. The tip restraint 40 is preferably formed from a single piece of thermoformed plastic. The tip restraint 40 includes a base section 42 into which the catheter tip 16 is placed and a cover section 44 which assists in retaining the catheter tip 16 in the preferred preformed shape within the base section 42. The base section 42 and the cover section 44 of the tip restraint 40 are interconnected by a hinge member 46 which is designed to move the cover section 44 away from the top surface 56 of the base section 42.

As generally illustrated in FIG. 1, the depth of the distal pocket 36 is chosen so that when the cover section 44 of the tip restraint 40 is folded over the top surface 56 of the base section 42, the height of the tip restraint 40 will extend slightly beyond the top surface of the tray 24 to allow the sealed envelope pouch 22 to contact the cover section 44 of the tip restraint 40 to assist in retaining the tip restraint 40 in the folded condition during storage. The width of the tip restraint 40 is chosen so that the tip restraint 40 will slide longitudinally in the distal pocket 36 and will be retained within the distal pocket 36 upon removal of the catheter 10 from the package.

Figure 3:
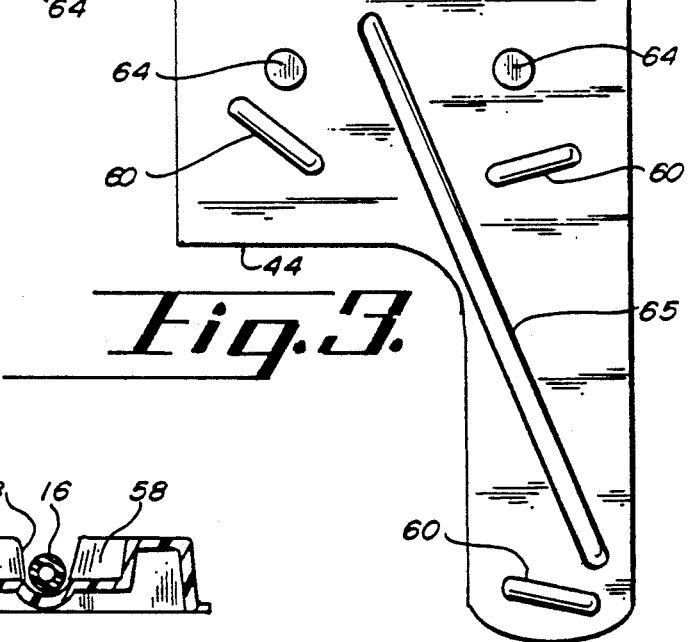
FIG. 3 is a frontal elevation view of an unfolded tip restraint of the type illustrated in FIG. 2.
Figure 4:
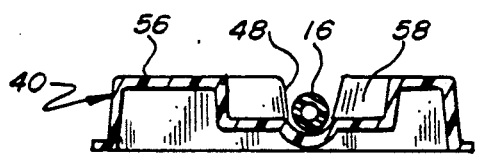
FIG. 4 is a side cross-sectional view of the type of tip restraint illustrated in FIG. 2 taken along lines 4—4 of FIG. 3.

As best illustrated in FIG. 3, the base section 42 of the tip restraint 40 includes an elongate and curved channel 48 which is shaped nearly identical to the desired preformed shape of the Left Amplatz type of catheter tip 16. The channel 48 of this embodiment, generally includes a primary surface of curvature 18 and a secondary surface of curvature 20. The sidewalls of the channel 48 adjacent to the shaft section 14 of the catheter 10 have a preferred draft angle of approximately 15°. As referred to herein, the draft angles are measured with respect to an imaginary reference line which is perpendicular to the bottom surface of the channel 48 so that a draft angle of 15° is oriented 105° from the bottom surface of the channel 48. The inner sidewall 50 of the channel 48 is located adjacent to the primary surface of curvature 18 and includes a primary bevel 52 having a preferred draft angle of approximately 30° and a secondary bevel 53 having a preferred draft angle of approximately 45°. The outer sidewall 54 of the channel 48 is located adjacent to the primary surface of curvature 18 and near the hinge member 46. The outer sidewall 54 is preferably oriented perpendicular to the top surface 56 of the base section 42. The remaining sidewalls of the channel 48 are located adjacent to the secondary surface of curvature 20 and have a preferred draft angle of approximately 15°.

Figure 2:
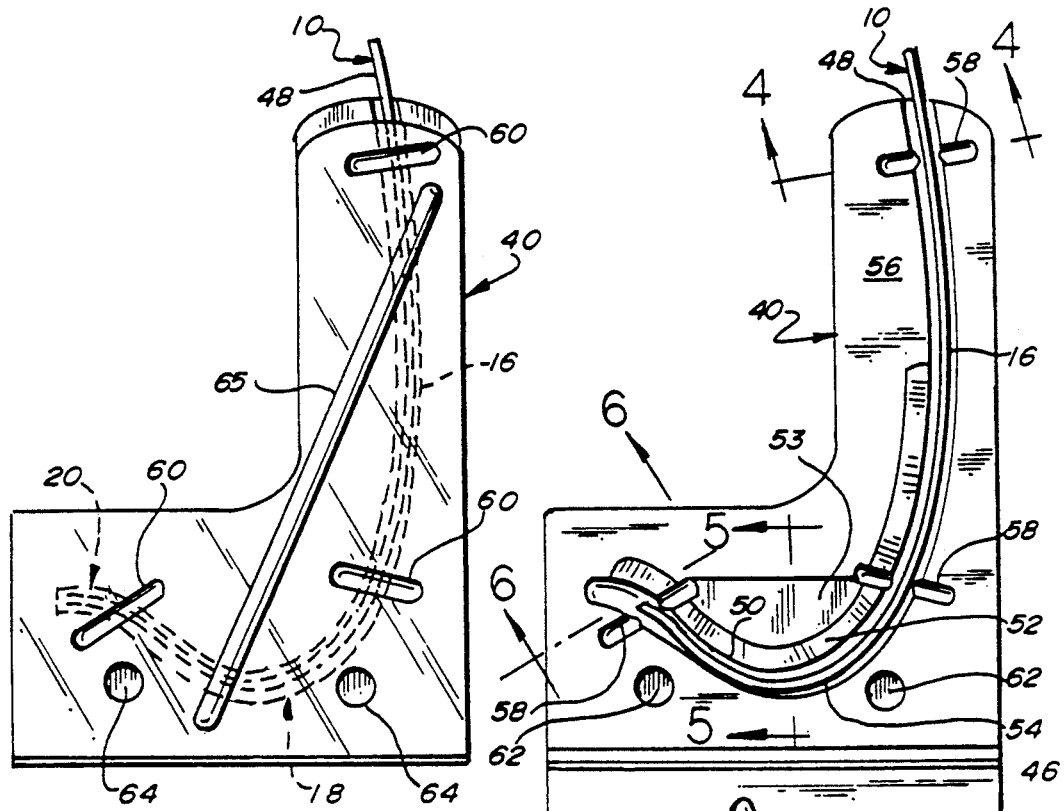
FIG. 2 is an enlarged frontal elevation view of the folded tip restraint of the present invention as illustrated in FIGS. 1 and 1A.

A plurality of recesses 58 on the base section 42 are oriented perpendicular to the lengthwise dimension of the channel 48 and extend downwardly from the top surface 56 of the base section 42 a sufficient distance so that when the male tabs 60 from on the cover section 44 are positioned in the recesses 58, the catheter tip 16 will be retained in the channel 48 of the tip restraint 40. A pair of circular recesses 62 are located on the base section 42 distally to the channel 48 to receive a pair of cylindrical friction tabs 64 from the cover section 44 therein. When the tip restraint 40 is folded, the friction tabs 64 are retained in the circular recesses 62. The friction tabs 64 and circular recesses 62 cooperate to resist the normal design of the hinge member 46 and prevent the tip restraint 40 from inadvertently opening until the envelope pouch 22 is opened. As illustrated in FIG. 2, the cover section 44 also includes a strengthening rib 65 to allow the tip restraint 40 to be manufactured using a relatively thin and lightweight thermoformed plastic material having sufficient rigidity to support the catheter tip 16 therein during sterilization and storage of the catheter 10.

In the preferred embodiment, the catheter 10 may expand or contract during sterilization and storage without affecting the overall shape of the preformed catheter 10. For example, if the shaft section 14 of the catheter 10 expands during sterilization, the tip restraint 40 will slide distally in the distal pocket 36 so that the shaft section 14 of the catheter 10 is not forced out of the lower linear channel 32. Additionally, the perpendicular outer sidewall 54 of the channel 48 will prevent relaxation of the catheter tip 16 during sterilization by limiting the expansion of the primary curvature section of the catheter tip 16 so that the catheter tip does not expand beyond the outer sidewall 54 of the primary surface of curvature 18.

Typically, when the nurse or physician desires to remove the catheter 10 from the sterile envelope pouch 22, they will separate the proximal end of the envelope pouch 22 so that the proximal pocket 26 of the tray 24 is exposed. Next, the hinged cover sheet 28 is opened to allow the physician to grasp and remove the hub fitting 12 of the catheter 10 from the proximal pocket 26. As the physician pulls on the hub fitting 12 of the catheter 10, the folded tip restraint 40 will slide proximally in the distal pocket 36 until the tip restraint 40 reaches the proximal end of the distal pocket 36. Further pulling on the catheter 10 causes the primary curvature section of the catheter tip 16 to ride up on the primary bevel 52 adjacent to the primary surface of curvature 18 in the channel 48. As this occurs, the upward pressure on the cover section 44 caused by the catheter tip 16 releases the friction tabs 64 from the circular recesses 62 and the design of the hinge means 46 will open the tip restraint 40 to release the catheter tip 16 from the channel 48. As the hinge means 46 opens the tip restraint 40, the catheter tip 16 will ride up on the secondary bevel 53 and completely release from the tip restraint 40 without being deformed.

Another embodiment of the tip restraint 70 of the present invention is illustrated in FIGS. 7-9. The tip restraint 70 of this embodiment is particularly adapted for use with an internal mammary artery bypass type of angiographic catheter. This type of catheter 72 is designed for the visualization of the coronary artery in the heart of a patient who has previously undergone bypass surgery with an internal mammary artery graft. This catheter 72 includes a hub member and shaft section similar to the hub fitting 12 and shaft section 14 of the catheter 10 illustrated in FIG. 1 and described above with respect to the preferred embodiment.

The tip restraint 70 of the present embodiment is designed for use in the tray 24 and envelope pouch 22 described above and generally includes an elongate base section 74 which is hingedly connected to a cover section 76 by a hinge member 78. The base section 74 of the present embodiment includes an elongate channel 80 having a gradually curved first section 82 and a second section 84 having a smaller radius of curvature. The sidewalls of the channel 80 of this embodiment include preferred draft angles similar to the preferred draft angles described above with respect to the preferred embodiment. The sidewalls adjacent to the first section 82 of the channel 80 have a preferred draft angle of approximately 15°. The outer sidewall 86 of the second section 84 is oriented perpendicular to the top surface 88 of the base section 74 so that the catheter tip 90 will not be forced out of the channel 80 during sterilization or storage of the present catheter 72. The inner sidewall 92 of the second section 84 includes first and second bevel sections, 94 and 96 respectively. The first and second bevel sections 94 and 96 have a preferred draft angle of approximately 30° to facilitate the removal of the catheter tip 90 from the tip restraint 70 when the user desires to remove the catheter 72 from the catheter package as described above.

As with the preferred embodiment, a plurality of female recesses 98 are oriented perpendicular to the channel 80 on the base section 74 of the tip restraint 70. The recesses 98 extend downwardly from the top surface 88 of the base section 74 a sufficient distance to retain the catheter tip 90 in the channel 80 when the male tabs 100 from the cover section 76 are inserted into the female recesses 98. A single circular recess 104 is positioned near the hinge member 78 of the present embodiment to receive a cylindrical friction tab 106 from the cover section 76 therein when the tip restraint 70 is folded. As illustrated in FIG. 7, the cover section 76 includes a strengthening rib 108 thereon. The rib 108 extends nearly the entire longitudinal length of the cover section 76 to allow the tip restraint 70 of the present embodiment to be manufactured using a relatively thin and lightweight thermoformed plastic material.

During sterilization or storage of the present embodiment, the tip restraint 70 will slide only distally or proximally within the distal pocket of the tray when the shaft section of the catheter 72 expands or contracts. When the user desires to remove the catheter 72 from the envelope pouch described above, they will separate the proximal end of the envelope pouch so that the proximal pocket of the elongate tray is exposed. Next, the hinged cover sheet is removed from the proximal pocket and the hub fitting of the catheter 72 is grasped and removed from the proximal pocket of the tray. As the user pulls the hub fitting of the catheter 72 from the package, the tip restraint 70 will be pulled proximally in the distal pocket of the tray until the tip restraint 70 reaches the proximal end of the distal pocket. Once the tip restraint 70 reaches the proximal end of the distal pocket, further pulling on the catheter 72 will cause the proximal section of the catheter tip 90 to straighten slightly. The distal section of the catheter tip 90 will then ride up the first and second beveled sections, 94 and 96 of the tip restraint 70. As the catheter tip 90 rides up the first and second beveled sections, 94 and 96, the male tab 100 is moved from the female recess 98 and the friction tab 106 is released from the circular recess 104. The design of the hinge member 78 will then cause the cover section 76 to move further from the top surface 88 of the base section 74 to completely release the catheter tip 90 from the tip restraint 70 and allow the catheter 72 to be removed from the package without causing permanent deformation of the catheter tip 90.

Figure 10:
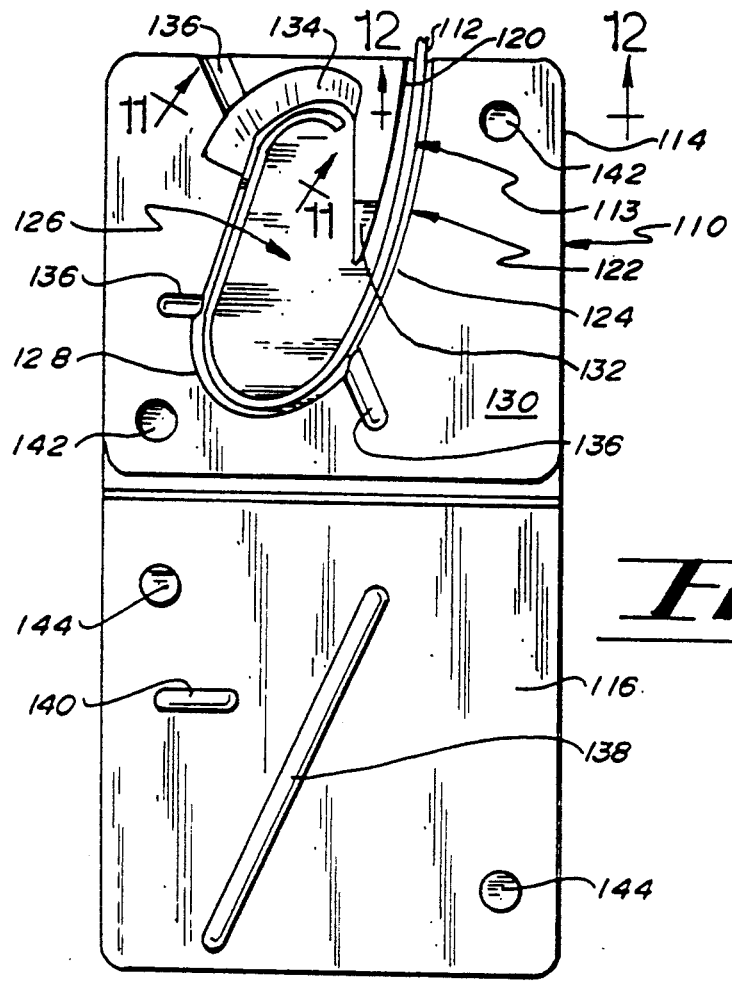
FIG. 10 is a frontal elevation view of an unfolded tip restraint of the present invention adapted for use with a left Judkins type of angiographic catheter.
Figure 11:
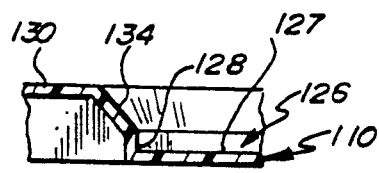
FIG. 11 is a side cross-sectional view of the tip restraint illustrated in FIG. 10 taken along lines 11—11 of FIG. 10.
Figure 12:
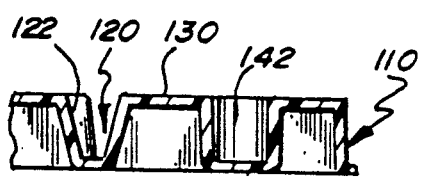
FIG. 12 is a side cross-sectional view of the tip restraint illustrated in FIG. 10 taken along lines 12—12 of FIG. 10.

Another form of the tip restraint 110 of the present invention is illustrated in FIGS. 10-12. The tip restraint 110 of this embodiment is particularly adapted for use with a Left Judkins type of angiographic catheter referred to herein generally as catheter 112. This type of angiographic catheter is typically the catheter of choice for the visualization of the coronary arteries in most patients. This type of catheter 112 includes a hub member (not shown) and a shaft section 113 similar to the hub fitting 12 and shaft section 14 of the catheter 10 illustrated in FIGS. 1 and 1A and described above with respect to the preferred embodiment of the present invention.

The tip restraint 110 of the present embodiment is designed for use in the tray 24 and envelope pouch 22 described above with respect to the preferred embodiment. The tip restraint 110 generally includes a base section 114 which is hingedly connected to a cover section 116 by a hinge member 118. The base section 114 of the present embodiment includes an elongate and recessed channel 120 having a relatively short first section 122 to retain the distal end of the shaft section 113 and the proximal end of the catheter tip 124 therein. The second section 126 of the channel 120 consists of an enlarged and generally oblong recess having a flat interior surface 137 and a circumferential sidewall 128 to releasably retain the distal end of the catheter tip 124 therein. The sidewalls of the first section 122 of the channel 120 include preferred draft angles of approximately 15°. As illustrated in FIG. 10, the distal side of the circumferential sidewall 128 is oriented perpendicular to the interior surface 127 of the second section 126 so that the catheter tip 124 will not be forced out of the channel 120 by relaxation of the catheter tip 124 during sterilization or storage of the present catheter 112. The proximal side of the second section 126 includes first and second bevel sections, 132 and 134, respectively, both of which have a preferred draft angle of approximately 30°. As illustrated in FIG. 10, the first bevel section 132 is located generally along the intersection of the first section 122 and the second section 126 of the channel 120. The second bevel section 134 is located along the proximal side of the circumferential sidewall 128. As with the preferred embodiment described above, the first and second bevel sections, 132 and 134 respectively, facilitate the removal of the catheter tip 124 from the tip restraint 110 by providing an angled surface on which the catheter tip 124 rides up to release the catheter tip 124 from the tip restraint 110 when the user desires to remove the present catheter 112 from the catheter package.

As illustrated in FIG. 10, a pair of recesses 136 are oriented along the circumferential sidewall 128 of the base section 114. The recesses 136 extend downwardly from the top surface 130 of the base section 114 so that the strengthening rib 138 and male tab 140 from the cover section 116 extend into the recesses 136 when the cover section 114 of the tip restraint 110 is folded over the top surface 130 of the base section 114. A pair of circular recesses 142 are located on the opposite corners of the base section 114 to allow a pair of cylindrical friction tabs 144 from the cover section 116 to be releasably retained circular recesses when the cover section 114 of the tip restraint 110 is folded.

During sterilization or storage of the present embodiment, the tip restraint 110 will slide distally or proximally within the distal pocket of the tray in response to the expansion or contraction of the shaft section 113 of the catheter 112. If the catheter tip 124 of the present embodiment relaxes during sterilization or storage of the catheter 112, the distal end of the catheter tip 124 will press against the proximal side of the circumferential sidewall 128 to retain the catheter tip 124 in the desired preformed shape.

When the user desires to remove the catheter 112 from the envelope pouch, they will separate the proximal end of the envelope pouch so that the proximal pocket of the elongate tray is exposed. Next, the hinged cover sheet is opened and the hub fitting of the catheter 112 is removed from the proximal pocket. As the user pulls the hub fitting from the proximal pocket, the tip restraint 110 will be moved proximally in the distal pocket of the tray until the tip restraint 110 reaches the proximal side of the distal pocket. When this occurs, continued pulling on the hub fitting of the catheter 112 will cause the catheter tip 124 to temporarily deform and ride up the first bevel section 132. As the catheter tip 124 rides up the first bevel section 132, the strengthening rib 138 and male tab 140 will be moved from the recesses 136. Next, the friction tabs 144 will be released from the circular recesses 142. The design of the hinge member 118 will cause the tip restraint 110 to open to allow the distal end of the catheter tip 124 to ride up the second bevel section 134 without being deformed by the circumferential sidewall 128 of the tip restraint 110.

Figure 13:
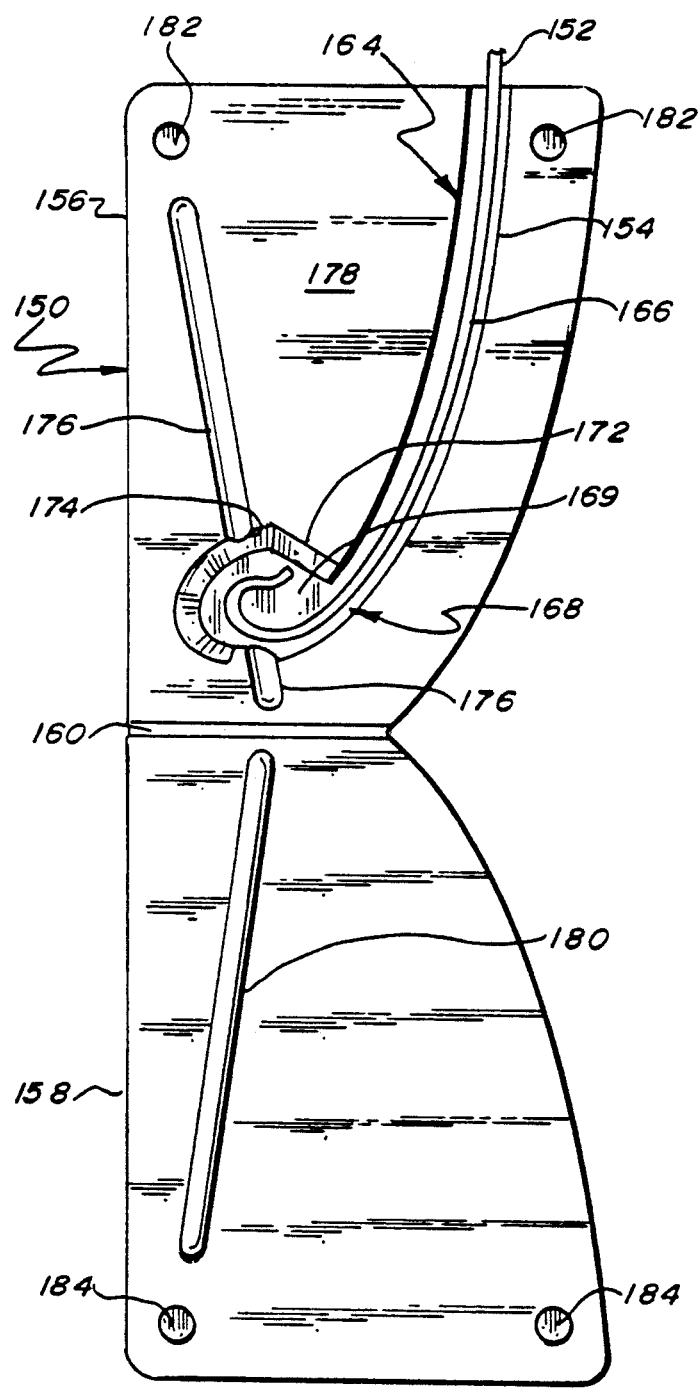
FIG. 13 is a frontal elevation view of an unfolded tip restraint of the present invention adapted for use with a left femoral ventricular type of angiographic catheter.

A further form of the tip restraint 150 of the present invention is illustrated in FIG. 13. The tip restraint 150 of this embodiment is particularly adapted for use with a left femoral ventricular type of catheter referred to herein generally as catheter 152. This type of catheter 152 is particularly adapted for use in visualizing the left ventricle of the heart of a patient. The catheter 152 includes a proximal hub member (not shown) and shaft section 154 similar to the hub fitting 12 and shaft section 14 of the catheter 10 as illustrated in FIGS. 1 and 1A and described above with respect to the preferred embodiment of the present invention.

The tip restraint 150 of the present embodiment is particularly adapted to be used in the tray 24 and envelope pouch 22 described above. The tip restraint 150 generally includes a base section 156 which is hingedly connected to a cover section 158 by a hinge member 160. The base section 156 of the present embodiment includes an elongate and recessed channel 162 having a relatively long and slightly curved first section 164 which is adapted to retain the distal end of the shaft section 154 of the catheter 152 and the proximal end of the catheter tip 166 therein. The second section 168 of the channel 162 consists of an enlarged and generally oblong recess having a flat interior surface 169 and a circumferentially extending sidewall 170 to releasably retain the distal end of the catheter tip 166 therein. The sidewalls of the first section 164 of the channel 162 include preferred draft angles of approximately 15°. The distal side of the circumferentially extending sidewall 170 is oriented perpendicular to the interior surface 169 of the second section 168 so that the catheter tip 166 of the catheter 152 will not be forced out of the channel 162 by the relaxation of the catheter tip 166 during sterilization or storage of the catheter 152. The proximal side of the second section 162 includes first and second bevel sections 172 and 174, respectively, both of which have a preferred draft angle of approximately 30°. The first bevel section 172 is preferably oriented perpendicular to the distal end of the catheter tip 166. The second bevel section 174 is oriented generally perpendicular to the first bevel section 172 along the proximal side of the circumferentially extending sidewall 170. As with the previous embodiments of the present invention, the first and second bevel sections, 172 and 174, respectively, facilitate the removal of the catheter tip 166 from the tip restraint 150 by providing an angled surface on which the catheter tip 166 is able to ride up when the user desires to remove the catheter 152 from the package.

As illustrated in FIG. 13, a pair of recesses 176 extend inwardly from the top surface 178 of the base section 156 so that the strengthening rib 180 from the cover section 158 extends into the second section 168 of the channel 162 when the cover section 158 is folded over the base section 156. A pair of circular recesses 182 are located adjacent to the proximal corners of the base section 156. The circular recesses 182 are oriented to retain a pair of cylindrical friction tabs 184 from the cover section 158 therein to releasably retain the cover section 158 adjacent to the top surface 178 of the base section 156 when the tip restraint 150 is folded.

When the user desires to remove the catheter 152 of the present embodiment from the tip restraint 150, they will separate the envelope pouch as described above and begin removing the hub fitting of the catheter from the proximal pocket of the tray. As the user removes the hub fitting of the catheter 152 from the tray, the tip restraint 150 will be pulled proximally in the distal pocket of the tray until the tip restraint 150 reaches the proximal end of the distal pocket. Continued pulling on the catheter 152 will cause the shaft section 154 of the catheter 152 to straighten and begin to leave the first section 164 of the channel 162. Further pulling on the catheter 152 will cause the catheter tip 166 to ride up the first and second bevel sections, 172 and 174 respectively, until the strengthening rib 180 is moved from the recesses 176. Once this occurs, further pulling on the catheter 152 will cause the friction tabs 184 to be released from the circular recesses 182. The design of the hinge member 160 will then cause the tip restraint 150 to unfold to allow the catheter tip 166 to be removed from the tip restraint 150 and catheter package without substantial or permanent deformation of the catheter tip 166.

The foregoing is intended to be descriptive of the preferred form of the embodiments described above. It should be understood that certain features of the above-identified embodiments may be modified without departing from the scope of the present invention which is defined by the following claims.

What is claimed is:

1. A catheter package including a catheter tip restraint to retain the preformed tip of a catheter in a predetermined shape, the tip restraint of said catheter package comprising:
   a tip restraint having a base section and a cover section connected along a common hinge so that said base section and said cover section may move away from each other by rotating around said common hinge,
   said base section including an elongate and recessed channel therein, said channel having a bottom surface and at least one sidewall and forming a recess having a shape substantially similar to the desired shape of a preformed catheter tip, and
   said cover section being moveable with respect to said base section around said common hinge to retain the catheter tip in said channel in a first position opposed to said base section and movable by rotation around said common hinge to a second position spaced from said base section to allow the catheter tip to be removed from said channel in said base section, said cover section disjoining from said base section.

2. The catheter package of claim 1 wherein said sidewall of said channel includes a bevelled section extending away from said bottom surface of said channel at an angle greater than 90 degrees therefrom to provide a gradually more open channel moving away from said bottom surface, said beveled section to facilitate the removal of the catheter tip from said channel without substantial deformation of the preformed catheter tip.

3. The catheter package of claim 1 wherein said sidewall of said channel includes a section of said sidewall which is generally perpendicular to said bottom surface of said channel to retain the catheter tip in said channel during sterilization and storage of the catheter.

4. The catheter package of claim 1 wherein said tip restraint is slidable in at least a portion of an elongate tray in response to the expansion or contraction of the catheter during sterilization or storage of said catheter package.

5. The catheter package of claim 1 wherein said channel includes a circumferentially extending sidewall at least a portion of which is generally perpendicular to said bottom surface of said channel and a further section of which extends from said bottom surface of said channel at an angle greater than 90 degrees from said bottom surface.

6. The catheter package of claim 1 wherein said base section includes a generally flat top surface.

7. The catheter package of claim 1 wherein said base section and said cover section include at least one first recess member and a first tab means thereon which interact to retain the catheter tip in said channel when said cover section is in said first position.

8. The catheter package of claim 7 wherein said base section and said cover section include a further second recess member and a second tab means thereon which interact to releasably retain said cover section in said first position.

9. A catheter package including a catheter tip restraint to be slidably retained in an elongate tray member to retain a catheter having a catheter tip and a hub member thereon in a preformed shape during sterilization and storage thereof, said package comprising:
   an elongate tray member having an elongate and linear channel and a recessed area therein for the removable placement of a preformed catheter in said tray member.
   a tip restraint having a base section and a cover section, said tip restraint being slidable in said recessed area of said tray member,
   said base section including an elongate and recessed channel therein, said channel having a bottom surface and at least one sidewall extending therefrom to form a recess in said base section having a predetermined shape to maintain the desired shape of the catheter tip during sterilization and storage of said package, and
   said cover section interconnected with said base section to retain the catheter tip in said channel in a first position opposed to said base section wherein said cover section is adjacent to said channel and said cover section being movable with respect to said base section to a second position spaced from said base section wherein the catheter tip is removable from said channel and wherein at least a portion of said cover section is movable away from said base section, said cover section disjoining from said base section.

10. The catheter package of claim 9 wherein at least a portion of said sidewall of said channel is oriented at an angle greater than 90 degrees with respect to said bottom surface of said channel and wherein a further portion of said sidewall is oriented generally perpendicular to said bottom surface of said channel.

11. The catheter package of claim 9 wherein said base section and said cover section are connected by a hinge member which moves said cover section from said first position to said second position and said base section and said cover section further include a first tab and recess means thereon to releasably retain said cover section in said first position.

12. The catheter package of claim 11 wherein said base section includes a plurality of spaced recesses therein which intersect said channel and wherein said cover section includes a plurality of spaced tabs thereon to retain said catheter tip in said channel when said cover section is in said first position.

13. The catheter package of claim 9 wherein said catheter package further includes a sterilizable pouch which encloses said tray and said tip restraint and wherein said tray includes a further recess therein to releasably retain the hub member of the catheter therein.

14. A catheter tip restrain for maintaining the desired shape of a catheter tip of a catheter during sterilization and storage of a catheter, the tip restraint comprising:
a base section hingedly connected to a cover section wherein said cover section is movable with respect to said base section between a first position wherein the catheter tip is retained in said tip restraint and a second position wherein the catheter tip is removable from said tip restraint,
a recessed channel member in one of said base section or cover section, said channel member having a bottom surface and at least one sidewall adjacent thereto to retain said catheter tip in the desired shape therein, at least a portion of said sidewall extending from said bottom surface of said channel at an angle greater than ninety degrees, and
said base section and said cover section including a first tab and recess means thereon to releasably retain said cover section in said first position.

15. The catheter tip restraint of claim 14 wherein said channel member is said base section and said base section includes a plurality of spaced apart recesses thereon which intersect said channel and a plurality of downwardly extending spaced apart tabs on said cover section which interact with said recesses on said base section to retain the catheter tip in said channel when said cover section is in said first position.

16. A catheter package comprising:
a catheter having a hub fitting, a preformed catheter shaft section and a preformed catheter tip thereon,
an elongate tray member having distal and proximal recessed pockets therein and at least one elongate and linear recessed channel extending therebetween such that said hub fitting is removably retained in said proximal pocket and said shaft section is removably retained in said linear channel,
a tip restraint having a base section hingedly connected to a cover section and means for releasably retaining said catheter tip therein and wherein said tip restraint is slidably retained in said distal pocket of said tray member, and
a pouch member sterilely enclosing said catheter, said tray member and said tip restraint therein.

17. A catheter packaging comprising:
a catheter having a proximal end, a preformed catheter shaft section and a preformed catheter tip,
an elongate tray member having a shaft retaining means thereon for releasably retaining said catheter shaft section thereon, and
a tip restraint slidably positioned on said tray member and including a base section having an elongate and recessed channel therein to retain said catheter tip therein and said tip restraint further including a cover section hingedly connected to said base section by a hinge means such that said cover section is movable between a first position opposed to said base section, wherein said cover section is adjacent said channel in said base section to enclose said catheter tip therein, and a second position spaced from said base section, wherein said catheter tip is removable from said channel, said cover section disjoining from said base section.

18. A catheter package comprising:
a catheter having a hub fitting, a preformed catheter shaft section and a preformed catheter tip,
an elongate tray member having distal and proximal recessed pockets therein and at least one elongate and linear recessed channel extending therebetween such that said hub fitting is removably retained in said distal pocket and said shaft section is removably retained in said linear channel,
a tip restraint slidably positioned in said distal pocket and including a base section hingedly connected to a movable cover section by a hinge member,
an elongate and nonlinear recessed channel on said base section to retain said catheter tip therein when said cover section is in a first position wherein said cover section is adjacent to said base section and encloses at least a portion of said channel to retain said catheter tip in said base section,
a first tab and recess means on said base section and cover section to releasably retain said catheter tip in said channel and a second tab and recess means on said base section and cover section to frictionally retain said cover section in said first position, and
said hinge member moving said cover section from said first position to second position wherein said catheter tip is removable from said channel and said tip restraint.

19. A catheter package including a catheter tip restraint to retain the preformed tip of a catheter in a predetermined shape, the tip restraint of said catheter package comprising:
a tip restraint having a base section and a cover section,
said base section including an elongate and recessed channel therein, said channel having a bottom surface and at least one sidewall and forming a recess having a shape substantially similar to the desired shape of a preformed catheter tip, said sidewall of said channel including a bevelled section extending away from said bottom surface of said channel at an angle greater than 90 degrees therefrom to provide a gradually more open channel moving away from said bottom surface, said beveled section to facilitate the removal of the catheter tip from said channel without substantial deformation of the preformed catheter tip, and
said cover section being interconnected and moveable with respect to said base section to retain the catheter tip in said channel in a first position and movable to a second position to allow the catheter tip to be removed from said channel in said base section.

* * * * *